(12) United States Patent
Miyai

(10) Patent No.: US 9,568,396 B2
(45) Date of Patent: Feb. 14, 2017

(54) EXHAUST GAS ANALYZING APPARATUS

(71) Applicant: HORIBA, Ltd., Kyoto (JP)

(72) Inventor: Masaru Miyai, Kyoto (JP)

(73) Assignee: Horiba, Ltd., Kyoto (JP)

( * ) Notice: Subject to any disclaimer, the term of this patent is extended or adjusted under 35 U.S.C. 154(b) by 223 days.

(21) Appl. No.: 14/203,819

(22) Filed: Mar. 11, 2014

(65) Prior Publication Data
US 2014/0250976 A1 Sep. 11, 2014

(30) Foreign Application Priority Data
Mar. 11, 2013 (JP) .................................. 2013-048341

(51) Int. Cl.
G01M 15/10 (2006.01)
G01N 1/22 (2006.01)
G01N 1/38 (2006.01)

(52) U.S. Cl.
CPC .......... *G01M 15/108* (2013.01); *G01N 1/2247* (2013.01); *G01N 1/2252* (2013.01); *G01N 1/38* (2013.01); *G01N 2001/2255* (2013.01)

(58) Field of Classification Search
CPC ................ G01N 2001/028; G01N 2001/021; G01N 2001/022; G01N 1/2252; G01N 1/2247; G01N 1/38; G01N 2001/2255; G01M 15/108
(Continued)

(56) References Cited

U.S. PATENT DOCUMENTS 6,112,574 A * 9/2000 Hirano .................... G01F 1/704
                                                    73/23.31
6,200,819 B1 * 3/2001 Harvey ................ G01N 1/2252
                                                    422/83
(Continued)

FOREIGN PATENT DOCUMENTS

EP      1405989 A2    4/2004
JP      04-268440 A   9/1992
(Continued)

OTHER PUBLICATIONS

EESR dated Apr. 28, 2015 issued for European patent application No. 14 000 806.1, pp. 1-8.
(Continued)

*Primary Examiner* — Peter Macchiarolo
*Assistant Examiner* — Monica S Young
(74) *Attorney, Agent, or Firm* — Brooks Kushman P.C.

(57) ABSTRACT

The present invention is one that is, in an exhaust gas analyzing apparatus used together with a CVS mechanism, adapted to be able to make an analysis with high accuracy, and an analyzing mechanism is provided with: a target component concentration meter that measures a moisture-influenced concentration related value that is a value related to concentration of a measuring target component in a state of being influenced by moisture; and a moisture concentration meter that measures a moisture concentration related value that is a value related to concentration of the moisture, and adapted to, on the basis of the moisture concentration related value, eliminate the influence of the moisture from the moisture-influenced concentration related value to calculate each of the first concentration related value and the second concentration related value.

6 Claims, 4 Drawing Sheets

(58) Field of Classification Search
USPC .......................................................... 73/23.31
See application file for complete search history.

(56) References Cited

U.S. PATENT DOCUMENTS

| | | | |
|---|---|---|---|
| 6,387,706 B1 | 5/2002 | Eden | |
| 6,505,524 B1* | 1/2003 | Silvis | G01N 1/2252 73/863.03 |
| 2003/0071218 A1* | 4/2003 | Nakamura | G01N 21/3504 250/343 |
| 2003/0149536 A1* | 8/2003 | Silvis | G01F 25/0053 702/24 |
| 2004/0103727 A1* | 6/2004 | Erlach | F02M 25/035 73/863.01 |
| 2010/0000339 A1* | 1/2010 | Silvis | G01N 1/2252 73/863.01 |
| 2011/0252864 A1* | 10/2011 | Guenther | G01N 1/2252 73/23.31 |
| 2013/0317757 A1* | 11/2013 | Silvis | G01N 1/2247 702/24 |

FOREIGN PATENT DOCUMENTS

| | | |
|---|---|---|
| JP | 2000-314684 A | 11/2000 |
| JP | 2001-099781 A | 4/2001 |
| JP | 2003-215037 A | 7/2003 |
| JP | 2005-201853 A | 7/2005 |
| JP | 2006-284508 A | 10/2006 |
| JP | 2009-103689 | 5/2009 |
| JP | 2010-223702 A | 10/2010 |
| JP | 2011-106999 A | 6/2011 |

OTHER PUBLICATIONS

Ward W. Wiers et al, Carbon Dioxide (CO2) Tracer Technique for Model Mass Exhaust Emission Measurement, SAE Technical Paper Series, Society of Automotive Engineers, Warrendale, PA, US, No. 720126, Feb. 1, 1972, pp. 1-14.

Gas Phase Measurements, DieselNet Technology Guide—Measurement of Emissions, Mar. 1, 2007, pp. 1-9.

Office Action dated Dec. 13, 2016 issued for Japanese Patent Application No. 2013-048341, 4 pgs, No translation provided.

* cited by examiner

EXHAUST GAS ANALYZING APPARATUS

CROSS-REFERENCE TO RELATED APPLICATION

This application claims priority to JP Application No. 2013-048341, filed Mar. 11, 2013, the disclosure of which is incorporated in its entirety by reference herein.

TECHNICAL FIELD

The present invention relates to an exhaust gas analyzing apparatus that samples and analyzes a total amount of exhaust gas emitted from an internal combustion engine of an automobile or the like.

BACKGROUND

As disclosed in JP-A2009-103689, this sort of exhaust gas analyzing apparatus is used together with a constant volume sampling (CVS) mechanism that is configured to sample a total amount of exhaust gas emitted from an internal combustion engine, mix diluent gas such as air with the exhaust gas to produce mixed gas, and make a flow rate of the mixed gas constant.

Specifically, this exhaust gas analyzing apparatus is one that is provided with: a mixed gas containing bag that samples and contains the mixed gas; a diluent gas containing bag that samples and contains the diluent gas; and an analyzing mechanism that analyzes the gases contained in the respective containing bags to measure, for example, concentrations of measuring target components contained in the gases, and by subtracting the concentration of the measuring target component contained in the diluent gas from the concentration of the measuring target component contained in the mixed gas, makes a background correction to calculate concentration of the measuring target component contained in the exhaust gas.

According to the above-described exhaust gas analyzing apparatus, by diluting the exhaust gas emitted from the internal combustion engine, the concentration of moisture contained in the mixed gas can be reduced. This makes it less likely to cause condensation of the moisture, and therefore makes it possible to suppress a measurement error due to a gas concentration change caused by water condensation or a dissolution loss of a water-soluble component.

Meanwhile, to measure a fuel consumption ratio of a vehicle, it is necessary to measure the concentration of CO2, and to do so, for example, a non-dispersive infrared absorption (NDIR) method is used.

However, in future, it is expected that measurement accuracy required for the fuel consumption ratio measurement is increased, but the conventional measurement method cannot respond to the expectation. This is because moisture contained in exhaust gas, which has been considered to have no problem in conventionally required measurement accuracy, may cause an adverse influence in terms of a CO2 measurement level required in future.

Generally, in order to suppress the influence of moisture, a technique such as condensing the moisture to drain it is also possible; however, as described above, the CVS mechanism is based on the major premise that dilution prevents moisture from being condensed, and therefore it is also not possible to employ such a technique.

SUMMARY

Technical Problem

Therefore, the present invention is made in order to, in an exhaust gas analyzing apparatus used together with the CVS mechanism based on the premise that moisture is contained as gas, eliminate an influence of moisture contained in exhaust gas to enable the concentration or amount of a measuring target component to be analyzed with higher accuracy.

Solution to Problem

That is, an exhaust gas analyzing apparatus according to the present invention is one that is used together with a CVS mechanism that is configured to sample a total amount of exhaust gas emitted from an internal combustion engine, produce mixed gas by mixing diluent gas with the exhaust gas of which the total amount is sampled, and make a flow rate of the mixed gas constant, and provided with: a mixed gas containing bag that samples and contains the mixed gas; a diluent gas containing bag that samples and contains the diluent gas; and an analyzing mechanism that analyzes the mixed gas in the mixed gas containing bag to measure a first concentration related value that is a value related to concentration of a measuring target component contained in the mixed gas, analyzes the diluent gas in the diluent gas containing bag to measure a second concentration related value that is a value related to concentration of the measuring target component contained in the diluent gas, and on the basis of the first concentration related value and the second concentration related value, calculates a value related to concentration of the measuring target component contained in the exhaust gas.

Also, the analyzing mechanism is provided with: a target component concentration meter that measures a moisture-influenced concentration related value that is a value related to concentration of the measuring target component in a state of being influenced by moisture; and a moisture concentration meter that measures a moisture concentration related value that is a value related to concentration of the moisture, and on the basis of the moisture concentration related value, eliminates the influence of the moisture from the moisture-influenced concentration related value to calculate each of the first concentration related value and the second concentration related value.

Note that a value related to concentration here includes not only a value for calculating the concentration or a value (e.g., a quantity) calculated on the basis of the concentration, but also the concentration itself.

If so, on the basis of the moisture concentration related value measured by the moisture concentration meter, the first concentration related value and the second concentration related value can be calculated as values resulting from eliminating the influence of the moisture, and therefore the value related to the concentration of the measuring target component in the exhaust gas, which is calculated by subtracting the second concentration related value from the first concentration related value, can be obtained with higher accuracy.

Specific examples of the target component concentration meter that makes an effect of the present invention particularly noticeable include one that is provided with an NDIR method detector that, on the basis of an absorption spectrum obtained by an NDIR method, detects the target component contained in each of the containing bags.

Specific examples of the measuring target component include CO2.

Advantageous Effects of Invention

According to the present invention configured as described, in the exhaust gas analyzing apparatus used together with the CVS mechanism, the concentration related values of the measuring target components contained in the gases contained in the respective containing bags can be obtained as the values resulting from eliminating the influence of the moisture, and therefore the concentration or amount of the measuring target component contained in the exhaust gas can be analyzed with higher accuracy.

DESCRIPTION OF EMBODIMENTS

In the following, an exhaust gas analyzing apparatus 100 according to the present invention is described with reference to the drawings.

The exhaust gas analyzing apparatus 100 of the present embodiment is one that is used to measure, for example, the concentration of a measuring target component contained in exhaust gas emitted from an internal combustion engine such as an engine.

Figure 1:
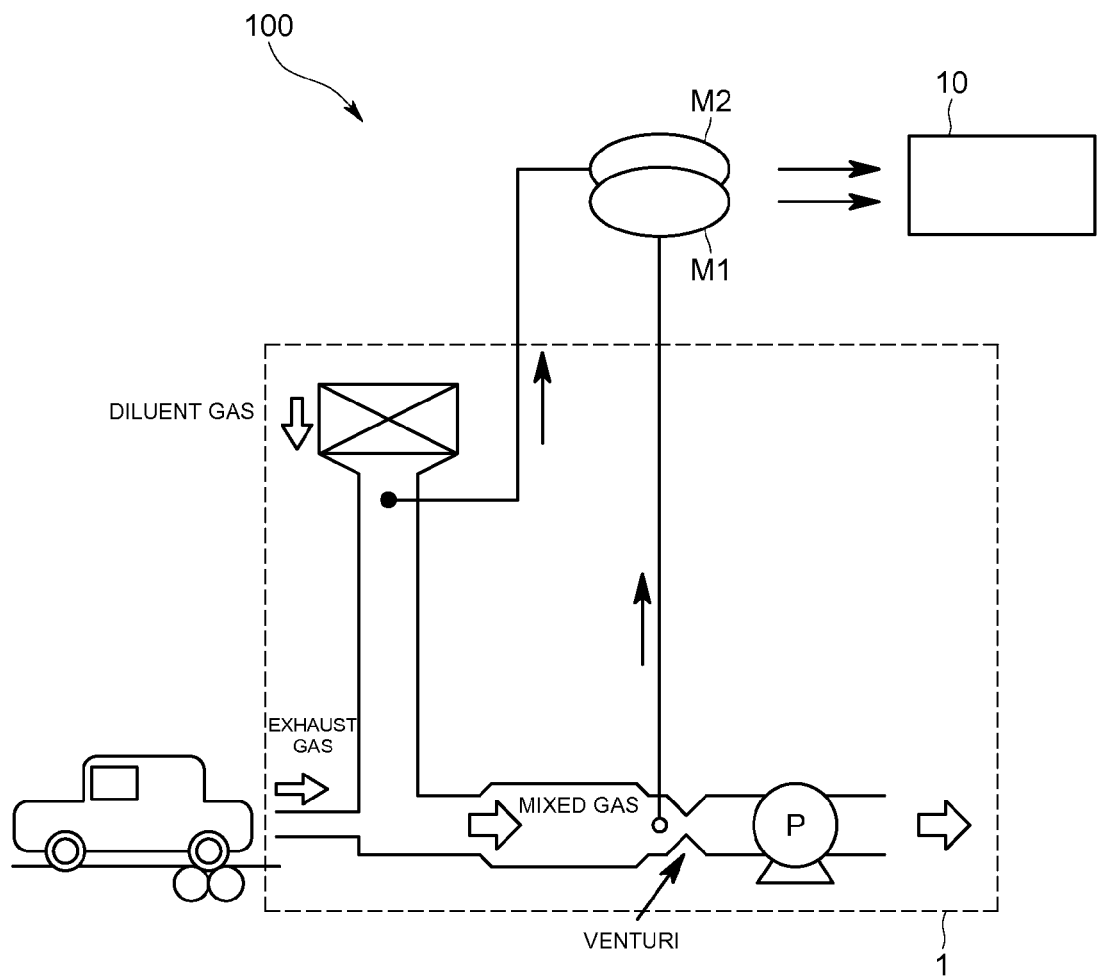
FIG. 1 is a diagram schematically illustrating a configuration of an exhaust gas analyzing apparatus of the present embodiment.

Specifically, the exhaust gas analyzing apparatus 100 is one that is, as illustrated in FIG. 1, used together with a constant volume sampling (CVS) mechanism 1 that is configured to sample a total amount of the exhaust gas, also produce mixed gas by mixing diluent gas with the exhaust gas of which the total amount is sampled, and make a flow rate of the mixed gas constant, and provided with: a mixed gas containing bag M1 that samples and contains the mixed gas; a diluent gas containing bag M2 that samples and contains the diluent gas; and an analyzing mechanism 10 that analyzes the gases contained in the bags to measure concentrations of the measuring target components contained in the gases, and on the basis of results of the measurement, calculates the concentration of the measuring target component contained in the exhaust gas.

The CVS mechanism 1 is, in this embodiment, one employing a critical flow venturi system for a flow rate control part, but may be one employing a constant volume pump system.

Figure 2:
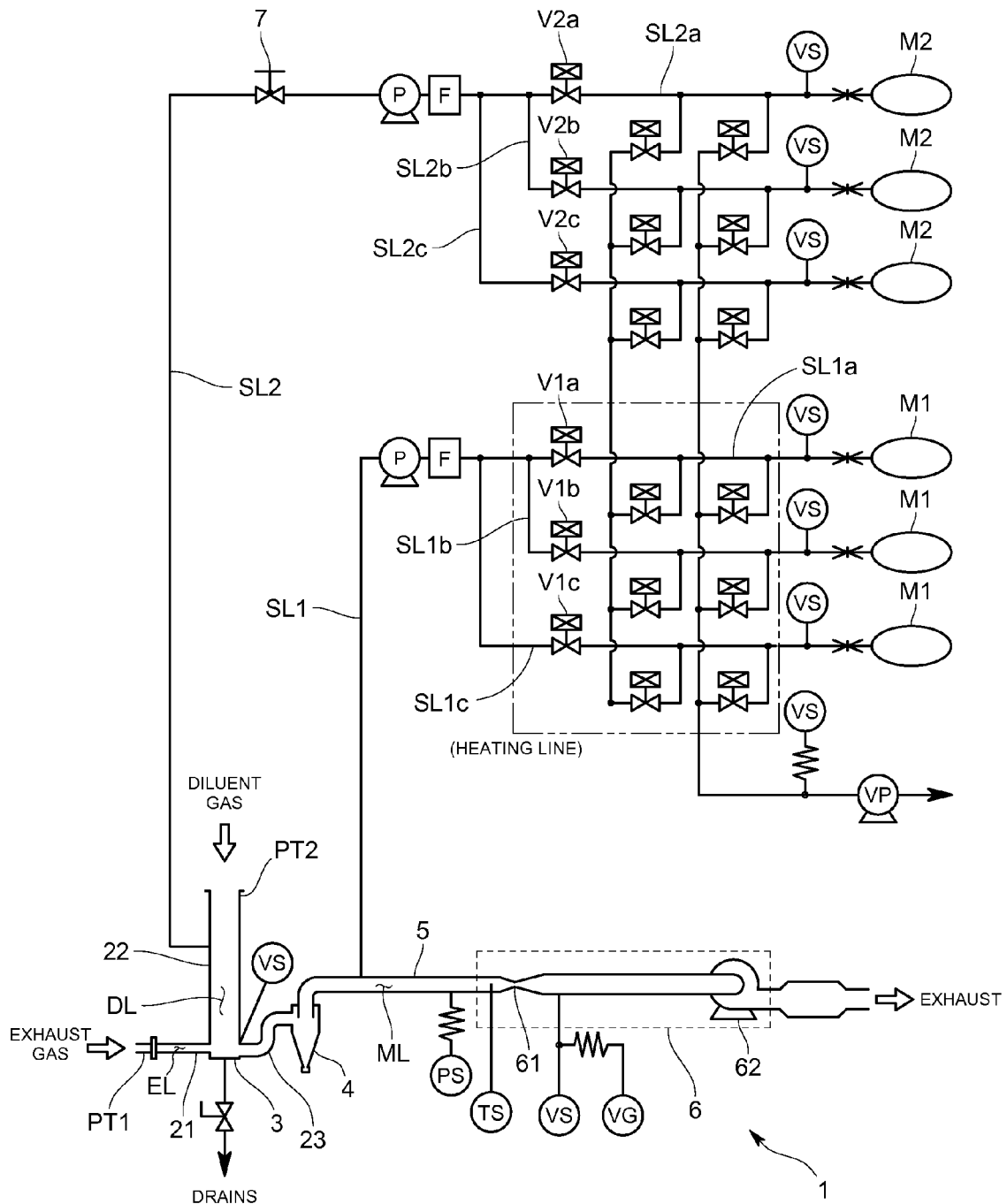
FIG. 2 is a diagram illustrating a specific configuration of a CVS mechanism of the same embodiment.

The CVS mechanism 1 is, as illustrated in FIG. 2, provided with: an exhaust gas flow path EL of which one end is connected to an exhaust gas introduction port PT1 for introducing the exhaust gas; a diluent gas flow path DL of which one end is connected to a diluent gas introduction port PT2 for introducing the diluent gas; and a mixed gas flow path ML that makes the exhaust gas flow path EL and the diluent gas flow path DL meet together, through which the mixed gas of the exhaust gas and the diluent gas flows.

The exhaust gas flow path EL is formed of an exhaust gas introduction pipe 21 of which one end is provided with the exhaust gas introduction port PT1 to introduce the exhaust gas, whereas the diluent gas flow path DL is formed of a diluent gas introduction pipe 22 of which one end is provided with the diluent gas introduction port, and other ends of the gas introduction pipes, where the exhaust gas flow path EL and the diluent gas flow path DL meet together, are connected to a mixer 3 that produces the mixed gas of the exhaust gas and the diluent gas. The mixed gas flow path ML is configured to include: a mixed gas introduction pipe 23 of which one end is connected with the mixer 3; a dust removing cyclone 4 that is connected to the mixed gas introduction pipe 23; a sampling pipe 5 that is connected to the cyclone 4; and a constant flow rate control part 6 that is connected to the sampling pipe 5.

The constant flow rate control part 6 is one that performs flow rate control so as to make constant a total flow rate of the exhaust gas introduced from the exhaust gas introduction pipe 21 and the diluent gas introduced from the diluent gas introduction pipe 22, and configured to include: a main venturi 61 that is connected downstream of the sampling pipe 5 and includes a critical flow venturi (CFV); and a suction pump 62 that is connected downstream of the main venturi 61, such as a blower. The suction pump 62 makes a differential pressure between pressures on upstream and downstream sides of the main venturi 61 equal to or more than a required value, and thereby the total flow rate is made constant. In addition, the mixed gas sucked by the suction pump 62 is discharged outside.

In a state where the total flow rate of the exhaust gas and the diluent gas, i.e., a flow rate of the mixed gas is made constant by the above-described CVS mechanism 1, the mixed gas is contained in the mixed gas containing bag M1 through a mixed gas sampling flow path SL1, and the diluent gas is contained in the diluent gas containing bag M2 through a diluent gas sampling flow path SL2.

The mixed gas sampling flow path SL1 is, at one end thereof, connected to the sampling pipe 5 constituting the mixed gas flow path ML, and on a downstream side, branches into a plurality of branched paths, and the other ends of the respective sampling branched paths SL1a to SL1c are connected to mixed gas containing bags M1. The respective sampling branched paths SL1a to SL1c are provided with on/off valves V1a to V1c for switching among the mixed gas containing bags M1 in which the sampled mixed gas is to be contained. Also, the mixed gas sampling flow path SL1 is heated by an external heater or the like, and configured to prevent moisture contained in the mixed gas from being condensed.

The diluent gas sampling flow path SL2 is, at one end thereof, connected to the diluent gas introduction pipe 22 constituting the diluent gas flow path DL, and on a downstream side, branches into a plurality of branched paths, and the other ends of the respective sampling branched paths SL2a to SL2c are connected to diluent gas containing bags M2. The respective sampling branched path SL2a to SL2c are provided with on/off valves V2a to V2c for switching among the diluent gas containing bags M2 in which the sampled diluent gas is to be contained. Also, on an upstream side of a branching point in the diluent gas sampling flow path SL2, a needle valve 7 for controlling a gas flow rate is provided.

The mixed gas contained in any of the mixed gas containing bags M1 and the diluent gas contained in any of the diluent gas containing bags M2 are supplied to the analyzing mechanism 10, where the concentrations of the measuring target components contained in the respective gases are measured.

Figure 3:
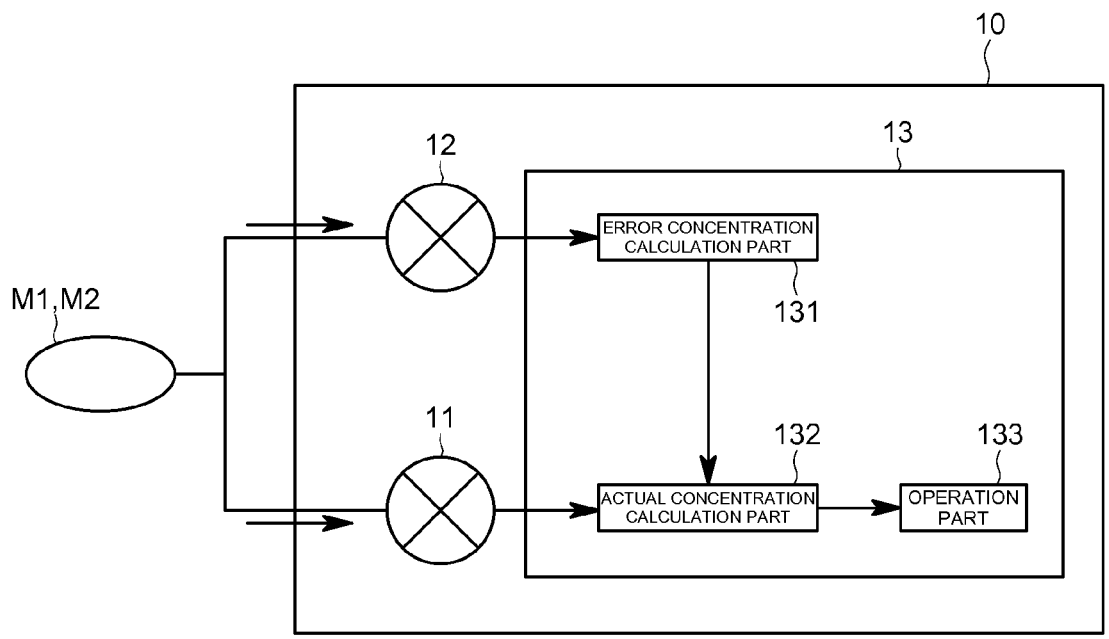
FIG. 3 is a diagram schematically illustrating a configuration of an analyzing mechanism of the same embodiment.

The analyzing mechanism 10 is one that is, as illustrated in FIG. 3, provided with: a target component concentration meter 11 that measures the concentrations of the measuring target components contained in the gases supplied from the respective containing bags M1 and M2; a moisture concentration meter 12 that measures concentrations of moisture contained in the gases; and an arithmetic unit 13 that obtains outputs respectively from the concentration meters to calculate the concentration of the measuring target component contained in the exhaust gas.

In addition, in the present embodiment, the measuring target component is set as $CO_2$.

Each of the target component concentration meter 11 and moisture concentration meter 12 is one that is, in the present embodiment, provide with an NDIR method detector, and irradiates each of the gases supplied to an unillustrated measurement cell with an infrared ray to, with the NDIR method detector, detect an absorption spectrum obtained by an NDIR method.

The target component concentration meter 11 is one that measures the concentration of $CO_2$ contained in each of the gases from a $CO_2$ absorption spectrum, and the moisture concentration meter 12 is one that measures the concentration of moisture contained in each of the gases from a moisture absorption spectrum.

A moisture absorption spectrum is not influenced by a $CO_2$ absorption spectrum; however, a $CO_2$ absorption spectrum is influenced by a moisture absorption spectrum, so that a $CO_2$ absorption spectrum measured by the target component concentration meter 11 is an absorption spectrum detected in a state of being influenced by the moisture contained in each of the gases, and $CO_2$ concentration measured from the absorption spectrum is calculated as moisture-influenced concentration that is influenced by the moisture.

The arithmetic unit 13 is physically an electric circuit configured to include, for example, a CPU, a memory, an AD converter, and the like. Also, the arithmetic unit 13 is functionally one that, in such a manner that the CPU and its peripheral devices cooperate according to a program stored in the memory, fulfills functions as: an error concentration calculation part 131 that calculates error concentrations, which are, of the moisture-influenced concentrations measured by the target component concentration meter 11, concentrations measured correspondingly to the influence of the moisture; an actual concentration calculation part 132 that calculates actual concentrations of the measuring target components contained in the mixed gas and the diluent gas; and an operation part 133 that operates the concentration of the measuring target component contained in the exhaust gas.

In the following, the respective parts are described in detail.

Figure 4:
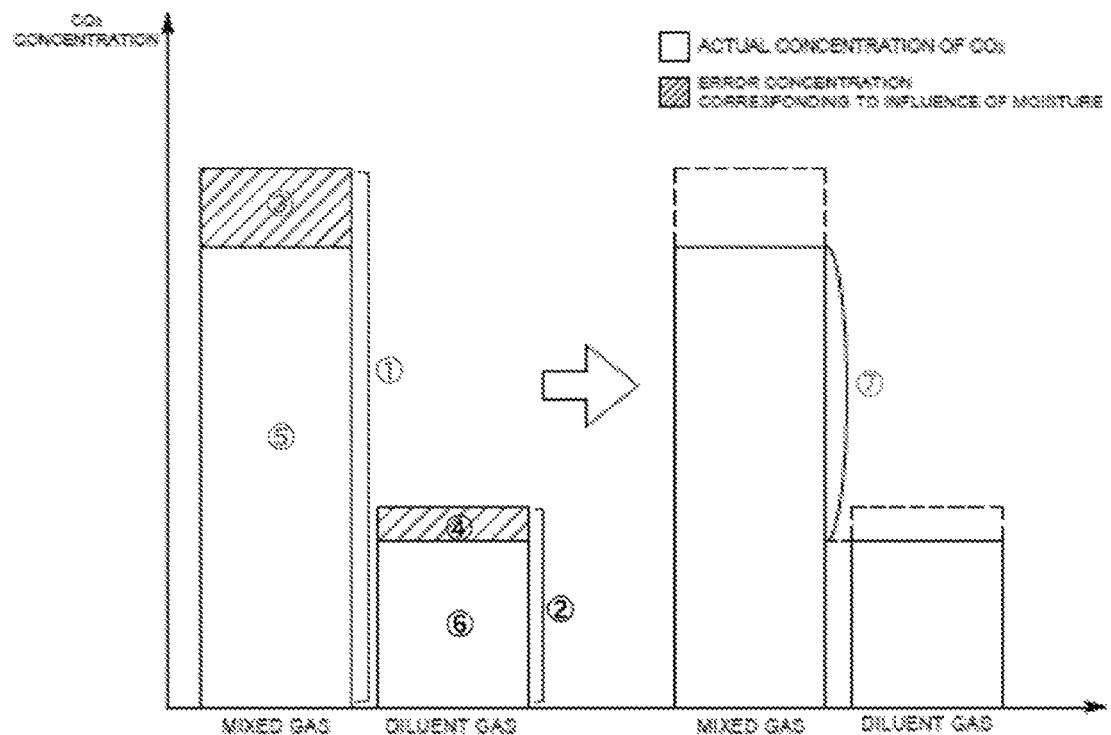
FIG. 4 is a graph illustrating measurement results by a target component concentration meter in the same embodiment.

As illustrated in FIG. 4, numbered item 1 is a graphical example of a first moisture-influenced concentration related value. Numbered item 2 is a graphical example of a second moisture-influenced concentration related value. Numbered item 3 is a graphical example of a first moisture concentration related value. Numbered item 4 is a graphical example of a second moisture concentration related value. Numbered item 5 is a graphical example of a first actual concentration related value. Numbered item 6 is a graphical example of a second actual concentration related value. And, numbered item 7 is a graphical example of a value related to concentration of the measuring target component contained in the exhaust gas.

Values measured by the target component concentration meter 11 indicate the concentrations influenced by the moisture (referred to as the moisture-influenced concentrations), and are values that are obtained by adding the error concentrations measured correspondingly to the influence of the moisture to the actual $CO_2$ concentrations contained in the gases.

Accordingly, the error concentration calculation part 131 obtains outputs from the moisture concentration meter 12, and on the basis of the concentrations of the moisture contained in the gases, calculates the error concentrations as a part of the $CO_2$ concentrations measured by the target component concentration meter 11, which is affected by interference in the moisture absorption spectra.

The actual concentration calculation part 132 obtains the outputs from the target component concentration meter 11 and signals from the error concentration calculation part 131, and as the actual $CO_2$ concentrations contained in the gases, which do not include the influence of the moisture, calculates the concentrations that are the moisture-influenced concentrations from which the error concentrations are correspondingly subtracted.

The operation part 133 obtains signals from the actual concentration calculation part 132 to operate the $CO_2$ concentration contained in the exhaust gas on the basis of the actual $CO_2$ concentrations contained in the mixed gas and the diluent gas.

More specifically, on the basis of the actual $CO_2$ concentrations contained in the gases, which are calculated in the actual concentration calculation part 132, $CO_2$ amounts contained in the gases are calculated. Specifically, the $CO_2$ amount contained in the mixed gas contained in the mixed gas containing bag M1 is calculated as a first concentration related value, and the $CO_2$ amount contained in the diluent gas contained in the diluent gas containing bag M2 is calculated as a second concentration related value. Then, by subtracting the second concentration related value from the first concentration related value, a background correction is made to calculate a $CO_2$ amount contained in the exhaust gas, and on the basis of the $CO_2$ amount, the $CO_2$ concentration contained in the exhaust gas is operated.

In addition, $CO_2$ concentration is also used for fuel consumption ratio measurement of which accuracy has been required to be improved in recent years. That is, a total amount of $CO_2$ emission is calculated from $CO_2$ concentration, a diluent gas flow rate, and the like, and from a numerical value of a travel distance of a vehicle, a fuel consumption ratio (unit is, for example, km/l) is calculated and displayed.

The $CO_2$ concentration is calculated with higher accuracy, and therefore a fuel consumption ratio can also be calculated with high accuracy.

According to the exhaust gas analyzing apparatus 100 according to the present embodiment configured as described above, in the exhaust gas analysis using the CVS method, by subtracting the error concentrations measured correspondingly to the influence of the moisture from the moisture-influenced concentrations measured by the target component concentration meter 11, the actual concentrations of the measuring target components contained in the gases can be calculated to analyze the concentration of the measuring target component contained in the exhaust gas with higher accuracy.

In particular, in the case of using the NDIR method to measure CO2 concentration contained in exhaust gas, the measurement has been influenced by uncondensed moisture in the past; however, according to the exhaust gas analyzing apparatus 100 according to the present embodiment, the influence of the moisture contained in the gases can be eliminated, and therefore the CO2 concentration can be measured with higher accuracy.

Note that the present invention is not limiter to the above-described embodiment.

For example, in the above-described embodiment, the target component concentration meter 11 and the moisture concentration meter 12 measure the concentrations of the measuring target components and the concentrations of the moisture contained in the gases; however, the present invention may be adapted such that the absorption spectra obtained from the concentration meters are outputted to the arithmetic unit 13, and the arithmetic unit 13 calculates the concentrations of the measuring target component and moisture.

Also, the present invention may be provided with pluralities of concentration meters 11 and 12 such that the mixed gas is supplied to corresponding target component concentration meter 11 and moisture concentration meter 12 and the diluent gas is supplied to corresponding target component concentration meter 11 and moisture concentration meter 12.

Configuring in this manner enables a measurement time to be shortened.

Further, in the above-described embodiment, the target component concentration meter 11 and the moisture concentration meter 12 respectively measure the concentrations of the measuring target component and the concentrations of the moisture; however, the present invention may be adapted to measure a quantity or volume that has a value related to concentration.

In addition, in the above-described embodiment, the measuring target component is CO2; however, the present invention may set another component such as CO as the measuring target component.

Besides, it should be appreciated that the present invention is not limited to any of the above-described embodiments, but can be variously modified without departing from the scope thereof.

REFERENCE SIGNS LIST

100: Exhaust gas analyzing apparatus
1: CVS mechanism
10: Analyzing mechanism
M1: Mixed gas containing bag
M2: Diluent gas containing bag
DL: Diluent gas flow path
ML: Mixed gas flow path
22: Diluent gas introduction pipe
23: Mixed gas introduction pipe
6: Constant flow rate control part
11: Target component concentration meter
12: Moisture concentration meter
13: Arithmetic unit

What is claimed is:

1. An exhaust gas analyzing apparatus that is used together with a CVS mechanism that is configured to sample a total amount of exhaust gas emitted from an internal combustion engine, produce mixed gas by mixing diluent gas with the exhaust gas of which the total amount is sampled, and make a flow rate of the mixed gas constant, the exhaust gas analyzing apparatus comprising:

a mixed gas containing bag that samples and contains the mixed gas;

a diluent gas containing bag that samples and contains the diluent gas; and an analyzing mechanism including a target component concentration meter that measures a first moisture-influenced concentration related value that is a value related to concentration of a measuring target component contained in the mixed gas, and that measures a second moisture-influenced concentration related value that is a value related to concentration of the measuring target component contained in the diluent gas, a moisture concentration meter that measures a first moisture concentration related value that is a value related to concentration of moisture associated with the mixed gas, and that measures a second moisture concentration related value that is a value related to concentration of moisture associated with the diluent gas, and, an arithmetic unit that calculates a first actual concentration related mixed gas value from the first moisture-influenced concentration related value and the first moisture concentration related value, that calculates a second actual concentration related diluent value from the second moisture-influenced concentration related value and the second moisture concentration related value, and that calculates a corrected value related to concentration of the measuring target component contained in the exhaust gas by subtracting the second actual concentration related diluent value from the first actual concentration related mixed gas value, wherein the corrected value related to concentration of the measuring target component contained in the exhaust gas is used for fuel consumption ratio measurement or adjustment of the diluent gas.

2. The exhaust gas analyzing apparatus according to claim 1, wherein the target component concentration meter is provided with an NDIR method detector that, on a basis of an absorption spectrum obtained by an NDIR method, detects the measuring target component contained in each of the containing bags.

3. The exhaust gas analyzing apparatus according to claim 1, wherein the measuring target component is $CO_2$.

4. A method for analyzing exhaust gas comprising:

measuring with a target component concentration meter a first moisture-influenced concentration related value that is a value related to concentration of a measuring target component contained in mixed gas from a mixed gas containing bag;

measuring a second moisture-influenced concentration related value that is a value related to concentration of the measuring target component contained in diluent gas from a diluent gas containing bag;

measuring with a moisture concentration meter a first moisture concentration related value that is a value related to concentration of moisture associated with the mixed gas;

measuring a second moisture concentration related value that is a value related to concentration of moisture associated with the diluent gas;

calculating with an arithmetic unit a first actual concentration related mixed gas value from the first moisture-influenced concentration related value and the first moisture concentration related value;

calculating a second actual concentration related diluent value from the second moisture-influenced concentration related value and the second moisture concentration related value; and calculating a corrected value related to concentration of the measuring target component contained in the exhaust gas by subtracting the second actual concentration related diluent value from the first actual concentration related mixed gas value, wherein the corrected value related to concentration of the measuring target component contained in the exhaust gas is used for fuel consumption ratio measurement or adjustment of the diluent gas.

5. The method of claim 4 further comprising detecting the measuring target component contained in each of the containing bags on a basis of absorption spectrum obtained by an NDIR method detector of the target component concentration meter.

6. The method of claim 4, wherein the measuring target component is $CO_2$.

* * * * *